United States Patent [19]

Krupin et al.

[11] Patent Number: 4,853,375

[45] Date of Patent: Aug. 1, 1989

[54] METHOD OF LOWERING INTRAOCULAR (EYE) PRESSURE

[75] Inventors: Theodore Krupin, Philadelphia; Richard A. Stone, Havertown, both of Pa.

[73] Assignee: The Trustees of the University of Pennsylvania, Philadelphia, Pa.

[21] Appl. No.: 97,554

[22] Filed: Sep. 16, 1987

[51] Int. Cl.$^4$ .............................................. A61K 31/65
[52] U.S. Cl. ..................................... 514/152; 514/913
[58] Field of Search ................................. 514/152, 913

[56] References Cited

U.S. PATENT DOCUMENTS 4,666,897  5/1987  Golub et al. ..................... 514/152
4,748,189  5/1988  Su et al. ........................... 514/781

Primary Examiner—Douglas W. Robinson
Assistant Examiner—Z. Fay
Attorney, Agent, or Firm—Caesar, Rivise, Bernstein, Cohen & Pokotilow, Ltd.

[57] ABSTRACT

A method of lowering intraocular pressure in the eye of a human or an animal, the method involving administering to the eye, an agent comprising an amount of tetracycline or a tetracycline related compound, such as demeclocycline, sufficient to achieve a significant lowering of intraocular pressure.

5 Claims, 3 Drawing Sheets

METHOD OF LOWERING INTRAOCULAR (EYE) PRESSURE

BACKGROUND OF THE INVENTION

This invention relates to the use of demeclocycline and other tetracycline derivatives for use in lowering intraocular pressure when applied to the eye.

The term "glaucoma" refers to a group of eye diseases affecting some 2% of the adult population. It is one of the three leading causes of acquired blindness in the developed world. Glaucoma develops because the pressure inside the eye (the intraocular pressure) becomes elevated above a level that can be tolerated safely. Within the eye, the ciliary processes secrete a clear fluid called aqueous humor. This field is essential for the nutrition of the lens and cornea of the eye. This aqueous humor drains through the trabecular meshwork, against a moderate resistance. The circulation and resistance to drainage of this fluid generates the intraocular pressure. Such intraocular pressure maintains the round shape of the eye and thus, provides for the eye's exquisite optical properties.

In glaucoma, a reduction in the drainage of aqueous humor elevates the intraocular pressure above normal level; this elevated intraocular pressure is transmitted throughout all tissues in the eye. The optic nerve, responsible for carrying the visual image from the light-sensitive retina to the brain, is damaged in glaucoma secondary to the elevated intraocular pressure. Because of impaired blood circulation and/or mechanical deformation that results from the abnormal pressures, the optic nerve undergoes an atrophic process and vision subsequently is reduced.

The various therapeutic approaches to glaucoma involve efforts to lower intraocular pressure either by reducing the rate at which aqueous humor is formed or by increasing the rate at which it leaves the eye. In the developed world where medications are accessible, the first approach to glaucoma therapy utilizes one or more drugs to achieve this result. When therapy with medications fails to lower intraocular pressure adequately, laser therapy or conventional surgical therapy is used next.

A wide range of medications now are available to treat glaucoma. Some are administered topically as drops to the eye; others are systemic medications taken orally in pill form. In many but not all glaucoma patients, these medications can lower intraocular pressure to a safe range.

All available glaucoma medications have certain limitations. First, both topical and systemic medications have significant ocular side effects, depending on the specific drug. These include such problems as local irritation, drug-induced changes in the refractive error of the eye, and increased risk of retinal detachment. Some medications make the pupils so small that they limit light entrance into the eye and cause difficulty with vision.

Systemic side effects also are prominent in some patients. Medications currently in use may alter serum electrolytes, appetite, mental status and the like. Even some medications used topically as drops can be absorbed into the blood and cause serious systemic side effects in susceptible individuals. Examples of side effects from drop therapy include extra heartbeats, cardiac failures, gastrointestinal symptoms and exacerbation of underlying asthma. All anti-glaucoma medications have limited duration of action; both topical and systemic medications require application at least once daily, and some require four times a day usage.

Because of ocular/systemic side effects and the limited duration of action, a major problem in the use of anti-glaucoma medications is poor patient "compliance". The term "compliance" refers to the tendency of patients to use their medications as instructed by the physician.

Because of the proved effectiveness of anti-glaucoma drug therapies and because of the higher risks of laser and surgical therapies, the search continues for new drugs to treat glaucoma.

Attention is now called to the various Figures of the drawings wherein:

FIG. 1 relates to the use of Desmopressin and is a dose response curve showing intraocular pressure rise at 6 hours after the intravenous administration of desmopressin in rabbits. Intraocular pressure is the mean of the 2 eyes from each rabbit. 8-10 animals at each desmopressin concentration;

FIG. 2 relates to the use of Desmopressin and is a time response curve showing the increase in intraocular pressure following intravenous administration of 100 mUnits/kg of desmopressin in 10 rabbits. Intraocular pressure is the mean of the 2 eyes from each rabbit;

Figure 5:
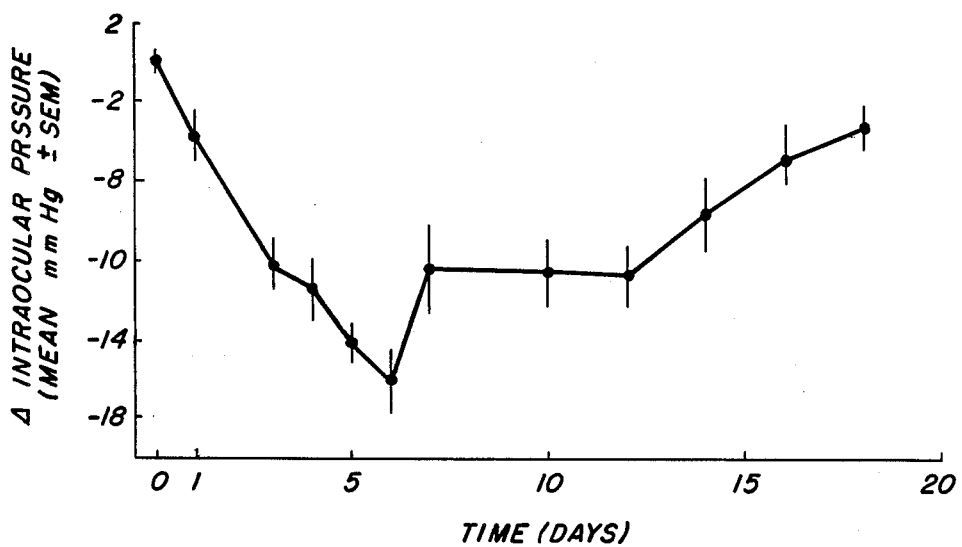

The drop in intraocular pressure (IOP) following intravitreal demeclocycline, 0.5 mg. Values represent [($IOP$ treated eye)] - ($IOP$ control eye)] for 12 rabbits; and FIG. 5 is a curve showing response of intraocular pressure to intravitreal demeclocycline in cats. The drop in intraocular pressure in repsonse to intravitreal injection, 0.2 mg., is shown 4 cats. Data represent [($IOP$ control eye) - ($IOP$ treated eye)].

DETAILED DISCUSSION - INITIAL EXPERIMENTS INVOLVING DESMOPRESSIN

A wide range of peptide hormones are known to influence intraocular pressure. Some of these hormones are present locally in the eye, being released by peptide-containing nerve fibers within the eye tissues. Others, such as vasopressin, are systemic hormones that reach the eye through the bloodstream.

Vasopressin (or antidiuretic hormone) is a nine amino acid peptide that is secreted into the blood. An intravenous infusion of vasopressin elevates intraocular pressure in rabbits. In the isolated iris-ciliary body preparation, vasopressin increases the short circuit current across the tissue, suggesting that vasopressin affects active sodium transport across the epithelium of the ciliary body.

Ocular studies with intravenous vasopressin are difficult. Vasopressin-mediated vasoconstriction elevates systemic blood pressure with secondary effects on intraocular pressure. Also, because of rapid enzyme hydrolysis by serum peptidases, the plasma half-life of vasopressin is only 5 to 10 minutes. To affect aqueous humor dynamics, vasopressin must be given by continuous infusion. To overcome these problems, the present inventors have studied the effect of intravenous desmopressin (1-deamino-8-D-arginine vasopressin) on aqueous humor dynamics in the rabbit. Desmopressin, a synthetic analog of vasopressin, is a highly specific antidiuretic agent exhibiting an antidiuretic to vasopressor activity ratio of 200:1 (vasopressin=0.9:1). In addition, desmopressin is not degraded by serum peptidases and has a 6 to 20 hour duration of action.

Such studies have been directed to the effect of desmopressin on intraocular pressure using awake rabbits weighing 2.5 to 4 kg, restrained in comfortable cloth wrappers or in specially designed plexiglass boxes. After topical 0.5% proparacaine anesthesia, intraocular pressure was measured with a pneumatonometer (Digilab Model 30R) manometrically calibrated against the rabbit eye.

After obtaining a stable baseline intraocular pressure measurement, desmopressin acetate (Armour Pharmaceutical Company, Kankakee, IL) was dissolved in filtered normal saline (osmolarity 295-305 mosmols/liter, pH 7.0) and was injected into a marginal ear vein at doses between 12.5 and 1000 mUnits/kg. Intraocular pressure was measured hourly during the first 8 hours and at 10 and 24 hours following injection. Tonography for measurement of aqueous humor outflow facility was performed in 9 rabbits with an electronic Schiotz tonometer just before and 5 hours after intravenous desmopressin (200 mUnits/kg). Episcleral venous pressure was measured with an episcleral venometer in 4 rabbits before and at various times after intravenous desmopressin (200 mUnits/kg). To study the effects of desmopressin on systemic blood pressure and blood chemistry, a femoral arterial catheter was placed in restrained awake animals using locally injected 1.0% lidocaine anesthesia. Systemic blood pressure was measured directly by connecting the cannula to a pressure transducer and a polygraph. Arterial blood sampels, obtained from the same cannula, were analyzed for $pO_2$, $pCO_2$, blood pH and plasma osmolarity with a Corning 16 5.5 pH blood gas analyzer and a Precision Instruments Osmette S automatic osmometer.

Aqueous humor samples for ascorbate and protein determination were obtained by posterior and anterior chamber paracentesis after topical 0.5% proparacaine anesthesia. Baseline chamber taps were done in one eye and intravenous desmopression (200 mUnits/kg) was administered. Intraocular pressure was remeasured, and posterior and anterior chamber taps were performed on the fellow eye either 1 or 5 hours later. Aqueous humor samples were immediately placed in 4.0% metaphosphoric acid and titrated with 2,6,dichlorophenol-indophenol for estimation of ascorbate concentration. The Kinsey-Palm formula was used to calculate the ascorbate ratio of the flow coefficient ($k_{fa}$) to the diffusion coefficient ($k_{dpa}$). In addition, anterior chamber aqueous humour protein concentration was measured using Biuret and Folin phenol reagents (Total Protein Kit No. 690, Sigma Chemical Co., St. Louis, MO).

Figure 1:
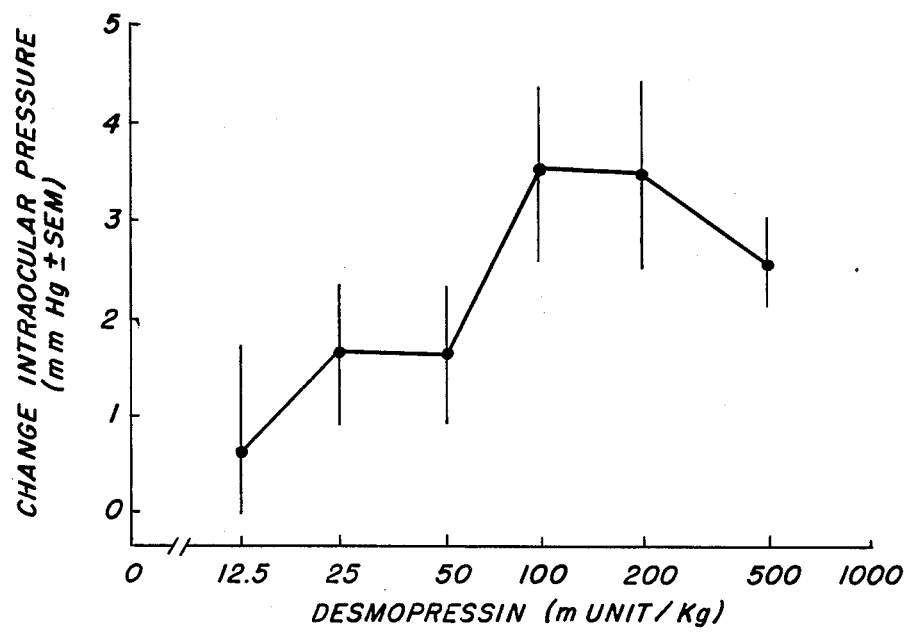
Figure 2:
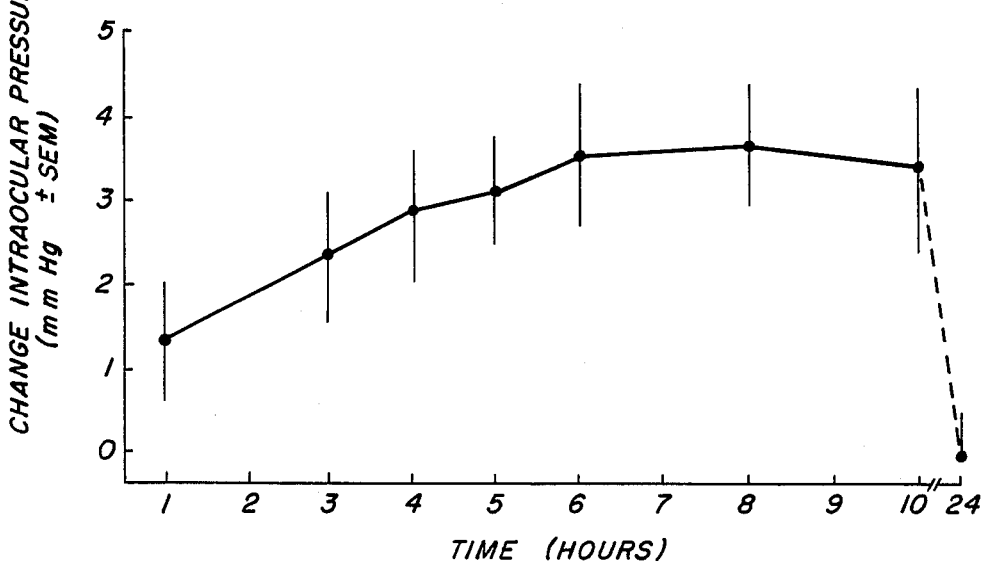

It was found (in parallel to previous reports by others who used vasopressin) that intravenously administered desmopressin caused a dose-dependent rise in intraocular pressure (FIG. 1). In general, desmopression induced an intraocular pressure rise that was statistically significant at 3 hours and rose steadily to peak at 6 to 8 hours after injection. The duration of the effect was 3 hours at the 12.5 mUnits/kg dose; higher doses caused a longer-lasting effect. At all doses tested, intraocular pressure returned to baseline by 24 hours after desmopressin injection. FIG. 2 shows the change in intraocular pressure after a dose of 100 mUnits/kg.

Baseline mean arterial blood pressure (106±4 mmHg) was not significantly altered 4 hours (107±2 mmHg, p>0.5), 5 hours (107±2 mmHg, p>0.5) or 6 hours (103±2 mmHg, p>0.5) following intravenous administration of 200 mUnits/kg desmopressin. Baseline arterial blood pH (7.40±0.01) was unchanged at 4 hours (7.43±0.02) and at 6 hours (7.44±0.03) after the same desmopressin dose. Plasma osmolarity (285.5±2.1 mOsm at baseline) was essentially unchanged at 4 hours (291.8±1.4, p>0.1; n=6) or at 6 hours (289.0±1.7, p>0.1; n=6).

Tonography showed no change in aqueous humor outflow facility (C) after 200 mUnits/kg of intravenous desmopressin despite a corresponding rise in intraocular pressure (Table 1). Using experimentally determined values of intraocular pressure, outflow facility and episcleral venous pressure, the aqueous humor flow rate was calculated using the Goldmann equation (Table 1). Five hours after desmopressin injection, calculated aqueous humor flow increased 57% (Table 1). Aqueous humor protein concentration was reduced slightly (Table 2), consistent with the increased flow; that aqueous humor protein content did not rise is evidence for the integrity of the blood-aqueous barrier after desmopressin infusion.

TABLE 1

Effects of Desmopressin (200 mU/kg I.V.) on Aqueous Humor Dynamics

|  | Baseline | 5-hour | Number of Animals |
|---|---|---|---|
| Intraocular pressure (mmHg) | 16.7 ± 0.8 | 19.2 ± 0.9* | 9 |
| Outflow facility (μl/min/mmHg) | .20 ± .03 | .22 ± .03 | 9 |
| Episcleral venous pressure (mmHg) | 8.3 ± 1.0 | 7.2 ± 0.2 | 4 |
| Calculated aqueous humor flow (μl/min)+ | 1.67 | 2.64 | 9 |

*Significant change from baseline value, paired t-test, p <0.01.
+Aqueous humor flow was calculated using the Goldmann equation, $F = (P_o - P_v)C$, where
F = aqueous humor flow in μl/min
$P_o$ = intraocular pressure in mmHg
$P_v$ = episcleral venous pressure in mmHg
C = aqueous humor outflow facility in μl/min/mmHg

TABLE 2

Effects of Desmopressin (200 mU/kg I.V.) on Aqueous Humor Chemistries

|  | Aqueous Humor cAMP (nM) | | Aqueous Humor Protein (mg/dl) | |
|---|---|---|---|---|
| Time After Injection | Mean ± S.E.M. | Number of Animals | Mean ± S.E.M. | Number of Animals |
| baseline | 15.2 ± 2.0 | 17 | 66 ± 10 | 9 |
| 1 hour | 12.5 ± 2.0[B] | 14 | | |

TABLE 2-continued

Effects of Desmopressin (200 mU/kg I.V.)
on Aqueous Humor Chemistries

| Time After Injection | Aqueous Humor cAMP (nM) | | Aqueous Humor Protein (mg/dl) | |
|---|---|---|---|---|
| | Mean ± S.E.M. | Number of Animals | Mean ± S.E.M. | Number of Animals |
| 5 hour | 10.2 ± 1.0[A] | 17 | 52.5 ± 3[A] | 9 | p values calculated from t-statistics using Student's t-test for paired data: [A]p < 0.05; [B]not significant from baseline measurement.

The baseline Kinsey-Palm $k_{fa}:k_{dpa}$ ratio was calculated using ascorbate measurements. The initial ratio of 2.12±0.23 increased 1 hour after intravenous injection of 200 mUnits/kg desmopressin to 3.14±0.47 (p<0.05; n=9). Five hours after intravenous drug administration, the $k_{fa}:k_{dpa}$ ratio (4.08±0.38) was also increased from baseline (2.94±0.32; p<0.01; n=6). The increased ascorbate ratios at 1 hour and at 5 hours are consistent with an increased flow of water into the eye.

In its primary action on the kidney in decreasing urine flow, vasopressin stimulates the production of the intracellular second messenger hormone, cyclic adenosine 3'5' monophosphate (cyclic AMP); this second messenger initiates a series of intracellular events that ultimately decrease urine flow. Desmopressin acts on the kidney in the same manner.

THE PRESENT INVENTION - FIRST ASPECT

The present invention in its first aspect relates to certain derivatives of the tetracycline series of antibiotics which inhibit the vasopressin-induced or desmopressin-induced stimulation of cyclic AMP in the kidney and thus, block the action of vasopressin on urine flow. Demeclocycline is the tetracycline derivative that has been found to be most effective in this renal action.

While it previously was reported that vasopressin has no effect on cyclic AMP levels in the ciliary processes in vitro, the present inventors have determined in vivo whether systemic desmopressin affected cyclic AMP levels in the aqueous humor of the eye. In 20 rabbits, anterior chamber aqueous humor samples were analyzed for cyclic AMP levels after acetylation using a cyclic AMP radioimmunoassay kit (DuPont Speciality Diagnostics, Boston, MA). A baseline sample was obtained from one eye. Desmopressin (200 mUnits/kg) was given intravenously, and aqueous humor of the fellow eye was sampled either 1 or 5 hours later. It was found that 1 hour after desmopressin administration, aqueous humor cyclic AMP showed a small reduction, not statistically significant. However 5, hours after desmopressin aqueous humor cyclic AMP was significantly reduced compared to baseline (Table 2). The decreased aqueous humor cyclic AMP, like the decreased aqueous humor protein content, is consistent with dilution from increased aqueous humor formation.

While there as no finding of an elevation of aqueous humor cyclic AMP, one still could not exclude an elevation in intracellular cyclic AMP in the ciliary process, undetected by the assay of extracellular intraocular fluids. Therefore, tests were run to determine whether demeclocycline influenced the effect of desmopressin in the eye, similar to demeclocycline's inhibition of vasopressin in the kidney. Awake rabbits were pretreated with oral demeclocycline hydrochloride (Sigma Chemical Co., St. Louis, MO, 20 mg/kg) 2 hours before intravenous desmopressin (200 mUnits/kg). Intraocular pressure was measured prior to pretreatment, just prior to intravenous injection of desmopressin (200 mUnits/kg) and then hourly for 8 hours. It was found that pretreatment with oral demeclocycline blocked the desmopressin-induced rise in intraocular pressure (Table 3).

The results from the foregoing indicate that systemic desmopressin, like vasopressin, elevates intraocular pressure in rabbits and that the elevation of intraocular pressure occurs because desmopressin stimulates the secretion of aqueous humor by the ciliary processes. The absence of effects on systemic blood pressure or serum osmolality indicate that desmopressin acts directly on aqueous humor secretion, although the precise mechanism of action of this synthetic hormone is still not fully elucidated. Further, these findings indicate that the tetracycline antibiotic derivative, demeclocycline, effectively blocks the desmopressin-induced rise in intraocular pressure, analogous to the effect of demeclocycline on the action of vasopressin in the kidney. Because there is no present evidence relating cyclic AMP to desmopressin/vasopressin effects on intraocular pressure, the precise cellular mechanism of action in the eye for demeclocycline remains to be established.

CESSATION OF THE USE OF DESMOPRESSIN

Tetracycline antibiotics have been used systemically for a great many years and have been used topically to treat superficial infections in the eye. These antibiotics as currently formulated penetrate poorly into the eye. See Hardberger, et al., Effects of Drug Vehicles on Ocular Uptake of Tetracycline, *Am J. Ophthalmol* 80:133–138 (1975) and Massey, et al., Effect of Drug Vehicle on Human Ocular Retention of Topically Applied Tetracycline, *Am J. Ophthalmol* 81:151–156 (1976). No effects on

TABLE 3

Effects of Demeclocycline Pretreatment on
Desmopressin-Induced Intraocular Pressure Rise*

| | Change in Intraocular Pressure (mmHg ± S.E.M.) | | | | |
|---|---|---|---|---|---|
| | Baseline IOP | 1-hour | 3-hour | 6-hour | Number of Animals |
| Desmopressin | 14.8 ± 1.0 | +1.4 ± 0.7 | +2.4 ± 0.8 | 3.6 ± 0.8 | 11 |
| Demeclocycline pretreatment | 16.8 ± 1.2 | +0.1 ± 0.2[A] | +0.3 ± 0.5[A] | 0.8 ± 0.3[A] | 7 |

TABLE 3-continued

Effects of Demeclocycline Pretreatment on
Desmopressin-Induced Intraocular Pressure Rise*

| | Change in Intraocular Pressure (mmHg ± S.E.M.) | | | |
|---|---|---|---|---|
| Baseline IOP | 1-hour | 3-hour | 6-hour | Number of Animals |
| (20 mg/kg PO) | | | | |

*Animals were pretreated with oral demeclocycline hydrochloride 2 hours before 200 mUnits/kg of intravenous desmopressin.
[A]Significant difference compared to desmopressin alone, $p < 0.05$, using Student's t-statistics; other values, not significant.

intraocular pressure have been reported. The present inventors undertook a series of studies, bypassing the poor ocular penetration of current formulations to address directly whether demeclocycline, tetracycline and other tetracycline related drugs affect intraocular pressure. In all subsequent studies described below, the use of desmopressin was omitted, and the direct effects of the tetracyclines on intraocular pressure were measured.

First, to access its direct effect on intraocular pressure, demeclocycline was administered intravitreally (10 μl/injection) in doses from 0.05 to 1.0 mg in rabbits, maintained in comfortable restraining boxes and with the use of topical proparacaine anesthesia. One eye received the drug and the contralateral eye received vehicle only as a control.

Figure 3:
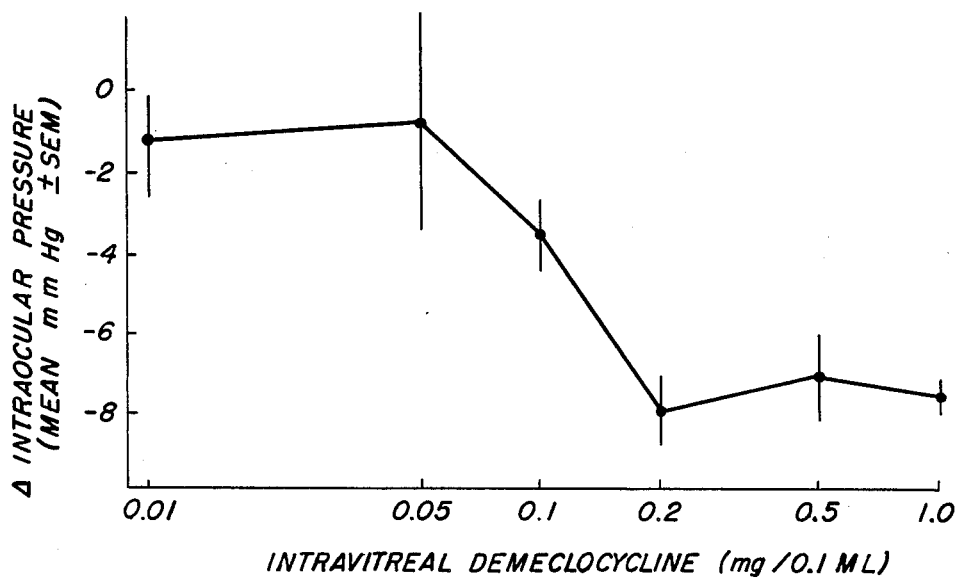
FIG. 3 shows the effect of intravitreal demeclocycline on intraocular pressure in rabbits and in particular, the change of intraocular pressure [($IOP$ control eye) - ($IOP$ treated eye)], 8 days after intravitreal injection. 8-14 animals at each demeclocycline concentration.
Figure 4:
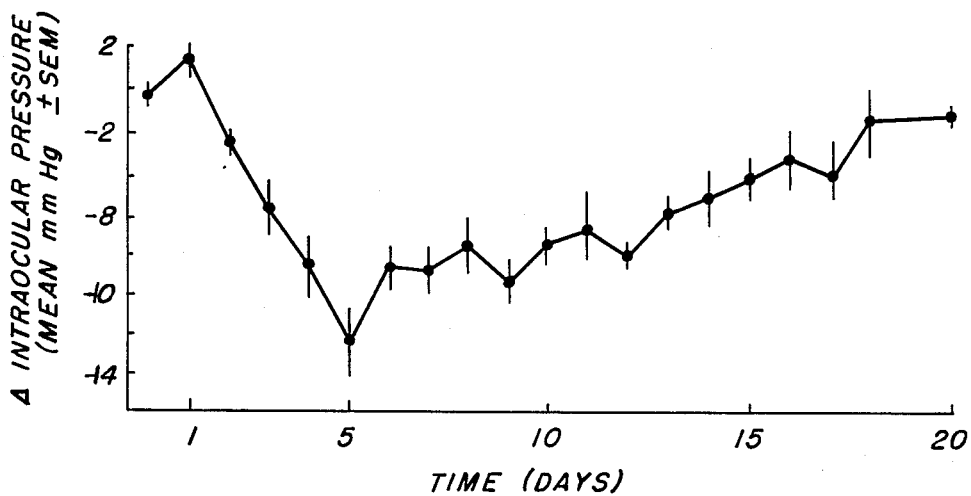
FIG. 4 is a curve showing time response to intravitreal demeclocyline.

Intravitreally administered demeclocycline caused a pronounced lowering of intraocular pressure, delayed in onset and prolonged in duration. FIG. 3 shows the dose response to intravitreal demeclocycline for doses ranging from 0.05 mg to 1.0 mg, as measured on day 8. Intravitreal demeclocycline 0.1 mg significantly ($p < 0.05$) lowered intraocular pressure for a duration of 6 days. Higher doses of demeclocycline resulted in a greater duration of intraocular pressure reduction with the maximum duration observed after a 0.5 mg dose with a significant ($p < 0.05$) reduction in intraocular pressure persisting for 16 days.

There were no evident adverse ocular effects from the intravitreal injection of demeclocycline. Pupil size remained unchanged. There were no signs of external irritation or redness. Slit-lamp evaluation showed no signs of intraocular inflammation in any animal. To study possible pathologic changes in the eye, 0.5 mg intravitreal injection of demeclocycline was given in one eye of a rabbit. At 6 days, intraocular pressure in the drug-treated eye fell 12 mmHg. The animal was sacrificed under deep phenobarbital anesthesia; both eyes were removed and studied by histopathological examination. There was no evident inflammation or other abnormality present in the drug-treated eye.

The means by which demeclocycline lowered intraocular pressure was studied (Table 4). For these investigations, rabbits received intravitreal injections of 0.2 mg demeclocycline in one eye, and the contralateral eye received vehicle as control. There was no change in aqueous humor outflow facility as determined by tonography. Aqueous humor flow was calculated as described above assuming a value of 8 mmHg for episcleral venous pressure; demeclocycline caused a 70% drop in aqueous humor flow rate. In addition, there was no significant alteration in aqueous humor protein concentration. The baseline Kinsey-Palm $K_{fa}:K_{dpa}$ ratio for ascorbate showed a significant 76 percent decrease in the drug-treated eye. All of these findings are consistent with intravitreal demeclocycline causing a significant reduction in the production of aqueous humor and lowering intraocular pressure on this basis.

TABLE 4

Ocular Effects of Intravitreal
Demeclocycline (0.2 mg) in Albino Rabbits

| | Drug Treated Eye | Vehicle/ Treated Eye | Number of Animals |
|---|---|---|---|
| Intraocular pressure (mmHg) | 11.1 ± 1.6[A] | 18.5 ± 1.7 | 6 |
| Aqueous humor outflow facility (μl/min/mmHg) | 0.21 ± 0.01[B] | 0.21 ± 0.02 | 6 |
| Calculated aqueous humor flow (μl/min)* | 0.65[A] | 2.20 | 6 |
| Aqueous humor protein (mg/dl) | 110 ± 17[B] | 77 ± 17 | 10 |
| $k_{fa}:k_{dpa}$ for ascorbate** | 1.22 ± 0.16[A] | 4.04 ± 0.87 | 10 |

Mean ± S.E.M.; t-statistics on the paired differences for drug treated vs. vehicle treated eye: [A]$p < 0.05$; [B]not significant.
*Aqueous humor flow was calculated using the Goldmann equation, $F = (P_o - P_v)C$; see Table 1.
**Calculated by the Kinsey-Palm equation.

No change in the intraocular pressure could be detected when demeclocycline was administered in the following ways: 1% or 2% solutions in physiological saline applied topically to 1 eye; 1% or 2% preparations in an ophthalmic ointment base applied topically to 1 eye; 20 mg/kg administered intravenously. The tetracycline class of drugs was known to penetrate the eye poorly, and it is believed the negative results with these other routes of administration are secondary to poor penetration into the intact eye of the formulations of these drugs at the doses studied.

The effects on intraocular pressure of other tetracycline drugs were determined. Each tetracycline drug was administered intravitreally in 1 eye at a dose of 0.2 mg, with the contralateral eye receiving vehicle only as a control. With only two exceptions, each of these agents induced a statistically significant lowering of intraocular pressure (Table 5). Even in these two cases, some activity was observed. Like demeclocycline, the maximum lowering of intraocular pressure did not occur until several days after intravitreal injection; the effects were prolonged for several days to over a week. Demeclocycline was the most effective agent tested in this series in terms of both degree and duration of intraocular pressure lowering effect.

To test the response of these agents in another animal, intravitreal demeclocycline (0.2 mg) was administered to 1 eye of 4 cats using the identical protocol (FIG. 5). The same results were obtained as in the rabbits. Intraocular pressure fell over several days reaching a minimum in 4 to 6 days. The maximum drop of intraocular pressure was in the range of 14–16 mmHg. Significant lowering of intraocular pressure persisted for several weeks.

TABLE 5
Effects of Tetracycline Derivatives on Intraocular Pressure (IOP) in Rabbits

| Compound (intravitreal injection-0.2 mg) | Max Effect* (mmHg) | Day of Lowest IOP** | Onset+ | Duration# | Number of Animals |
|---|---|---|---|---|---|
| Demeclocycline | 12.5 | 7 | 2 | 9 | 12 |
| Tetracycline | 6.9 | 4 | 1 | 5 | 6 |
| Oxytetracycline | 4.8 | 8 | 1 | 11 | 6 |
| Minocycline | 4.8 | 4 | 2 | 7 | 6 |
| Methacycline | 3.1 | 8 | 7 | 3 | 6 |
| Chlortetracycline | 2.8 | 2 | | | 6 |
| Doxycycline | 2.6 | 3–4 | | | 6 |

*Maximum decrease in IOP: IOP control eye minus IOP treated eye [($^{IOP}$control eye) - ($^{IOP}$treated eye)].
**Day of maximum decrease in IOP following intravitreal administration.
+First day the mean IOP in the treated eyes was significantly lower ($p < 0.05$) than the mean IOP in the control eyes, using t-statistics on paired data.
Number of days IOP was significantly lower ($p < 0.05$) in the treated than the control eye, using t-statistics on paired data.

While the present inventors have established that the tetracycline class of drugs depress the secretion of aqueous humor, the precise mechanism of action is currently not known. There is no evidence for a tonic vasopressin regulation of aqueous humor in the normal animal. It is believed that desmopressin is not acting strictly by inhibition of a baseline vasopressin effect. Presumably, these drugs interfere with a critical receptor or cellular process in the formation of aqueous humor.

In accordance with the present invention, most, if not all tetracycline derivatives effectively, lower intraocular pressure in rabbits. Similar results from initial studies in cats indicate that this phenomenon occurs in more than one species and suggest that these observations may well apply to man. The intraocular pressure lowering effect is delayed in onset, requiring several days to reach maximum effect. The intraocular pressure lowering effect is pronounced in degree; these agents are far more effective than most other intraocular pressure lowering drugs when studied in normal rabbits and cats. Based on the work in rabbit, no adverse ocular side effects were detected, and it is believed that these agents act specifically to suppress the formation of aqueous humor. The intraocular pressure lowering effect of these agents is prolonged; among the more effective agents of this class, significant intraocular pressure lowering persists after a single application for at least a week.

The tetracycline compounds described here have great potential value as anti-glaucoma therapy in humans. First, the effect of these agents is quite pronounced in the experimental animals studied. Second, the drugs have a long duration of action. No local ocular toxicity was observed. Further, these agents are currently used as systemic antibiotics and as topical ocular antibiotics. While the potential for allergic reaction exists for any drug, these agents do not exhibit the degree of systemic toxicity currently known to be present with other anti-glaucoma agents. Based on their pronounced effect on intraocular pressure, the long duration of their action and the low potential for local and systemic side effects from these agents, they may constitute a valuable new anti-glaucoma therapy.

The current available tetracycline agents for the treatment of glaucoma in man do not penetrate the eye well. However, it is contemplated that the active agents of the present invention can be formulated in an appropriate vehicle, such as drops, an ointment or some other preparation for topical application, although the active agent in some instances may be delivered systemically, by oral, intravenous or other route of administration. Studies have now been carried out using topical delivery means involving demeclocycline to demonstrate the activity of some alternative formulations. These will now be discussed.

EFFECT OF TOPICALLY ADMINISTERED DEMECLOCYCLINE ON INTRAOCULAR PRESSURE IN RABBITS

Demeclocycline was administered topically to one eye of rabbits. Because tetracycline drugs was known to penetrate poorly into the eye, two alternative formulations were made to attempt to enhance ocular penetration: ocular application of a soft contact lens presoaked in drug, and preparation of the drug in an ointment vehicle at a higher dose than previously discussed. Intraocular pressure was measured in awake and restrained rabbits using topical proparacaine hydrochloride anesthesia and a calibrated pneumatonometer, the identical protocol used elsewhere in the application.

DEMECLOCYCLINE-SOAKED CONTACT LENS

The administration of demeclocycline via a presoaked soft contact lens lowered intraocular pressure. The soft contact lens was soaked for one hour in a demeclocycline 1% (pH 6.8) solution. The lens was placed on one eye for one hour and then removed. Six rabbits were studied.

| | Intraocular Pressure, mean mmHg ± SEM, Following Demeclocycline Soaked Contact Lens | | | | |
|---|---|---|---|---|---|
| | | | Time After Removal of Contact Lens | | |
| Condition | Baseline | 5-hr. | 1-day | 2-day | 4-day |
| Treated Eye | 18.4 ± 2.0 | 19.0 ± 2.0 | 12.5 ± 2.0* | 13.5 ± 1.1* | 14.5 ± 1.4* |
| Control Eye | 18.2 ± 1.9 | 20.2 ± 1.6 | 19.2 ± 1.5 | 19.6 ± 1.6 | 18.8 ± 1.0 |

*Significantly different from control eye, paired-t test, $p < 0.05$.

DEMECLOCYCLINE OINTMENT

Demeclocycline ointment 5% (weight/weight in petroleum base) effectively lowered intraocular pressure following twice daily administration. The ointment was applied to one eye of ten rabbits twice daily for seven days and then stopped. The onset of intraocular pressure lowering was several days after the initiation of therapy and persisted as long as the ointment was given. Intraocular pressure returned to baseline values following termination of demeclocycline therapy.

| | Intraocular Pressure, mean mmHg ± SEM Following 5% Demeclocycline Ointment | | | | |
|---|---|---|---|---|---|
| | | Time After Initiation of Demeclocycline | | | |
| Condition | Baseline | 1-day | 3-days | 4-days | 5-days |
| Treated Eye | 21.0 ± 1.9 | 20.6 ± 1.3 | 20.01.2* | 14.6 ± 2.1* | 13.2 ± 1.6* |
| Control Eye | 21.2 ± 1.6 | 22.2 ± 2.3 | 23.4 ± 1.9 | 24.0 ± 2.3 | 23.2 ± 2.2 |

| | | | | Days After Stopping Ointment | |
|---|---|---|---|---|---|
| | 6-days | 7-days | Ointment | day-2 | day-6 |
| Treated | 15.4 ± 1.2* | 15.4 ± 1.4* | stopped | 19.4 ± 1.8 | 19.4 ± 0.4 |
| Control | 19.4 ± 0.7 | 22.4 ± 1.4 | | 22.4 ± 1.9 | 20.2 ± 0.6 |

*Significantly different from control eye, paired-t test, $p < 0.05$.

Without further elaboration, the foregoing will so fully illustrate our invention that others may, by applying current or future knowledge, adopt the same for use under various conditions of service.

We claim:

1. A method of lowering intraocular pressure in the eye of a human or an animal, said method comprising administering to said eye, a therapeutically effective amount of tetracycline or a derivative of the tetracycline series having the property to achieve a significant lowering of intraocular pressure in the eye.

2. The method of claim 1 wherein said agent comprises demeclocycline.

3. The method of claim 1 wherein said agent is applied topically to the eye in the form of an ointment, drops, or other suitable topical delivery system.

4. The method of claim 1 wherein said agent is delivered by way of an injection or intravenously or orally.

5. The method of claim 1 wherein said agent is selected from the group consisting of demeclocycline, tetracycline, oxytetracycline, minocycline, methacycine, chlorotetracycline and doxycycline.

* * * * *